United States Patent [19]

Tremulis

[11] Patent Number: 4,953,553

[45] Date of Patent: Sep. 4, 1990

[54] PRESSURE MONITORING GUIDEWIRE WITH A FLEXIBLE DISTAL PORTION

[75] Inventor: William S. Tremulis, Redwood City, Calif.

[73] Assignee: Advanced Cardiovascular Systems, Inc., Santa Clara, Calif.

[21] Appl. No.: 350,500

[22] Filed: May 11, 1989

[51] Int. Cl.$^5$ .............................................. A61B 5/00
[52] U.S. Cl. ..................... 128/637; 128/673; 128/657; 128/748; 128/772; 604/164; 604/280
[58] Field of Search ............... 128/637, 672, 673, 674, 128/675, 748, 772, 657; 604/95, 164, 170, 280, 282

[56] References Cited

U.S. PATENT DOCUMENTS 4,003,369  1/1977  Heilman et al. ...................... 128/772
4,582,181  4/1986  Samson ................................. 604/95

Primary Examiner—Randall L. Green
Assistant Examiner—Randy Shay
Attorney, Agent, or Firm—Fulwider, Patton, Lee & Utecht

[57] ABSTRACT

A pressure monitoring guidewire and method of using the same for a coronary procedure such as angioplasty, angiography, or valvuloplasty. The guidewire has a main tubular member and a more flexible tubular extension with one or more pressure monitoring ports on the distal end thereof. The distal end portion of the guidewire is advanced beyond the distal end of the dilatation catheter, with the pressure monitoring port in a portion of the coronary anatomy where pressure is to be monitored. With the guidewire so positioned, the pressure in the desired portion of the coronary anatomy is measured at the proximal end of the guidewire through the proximal opening in the main tubular member.

10 Claims, 4 Drawing Sheets

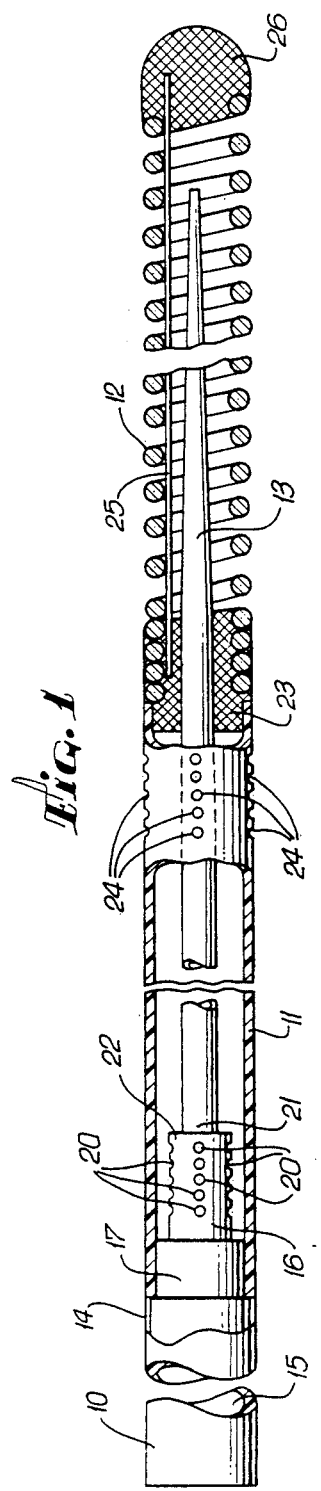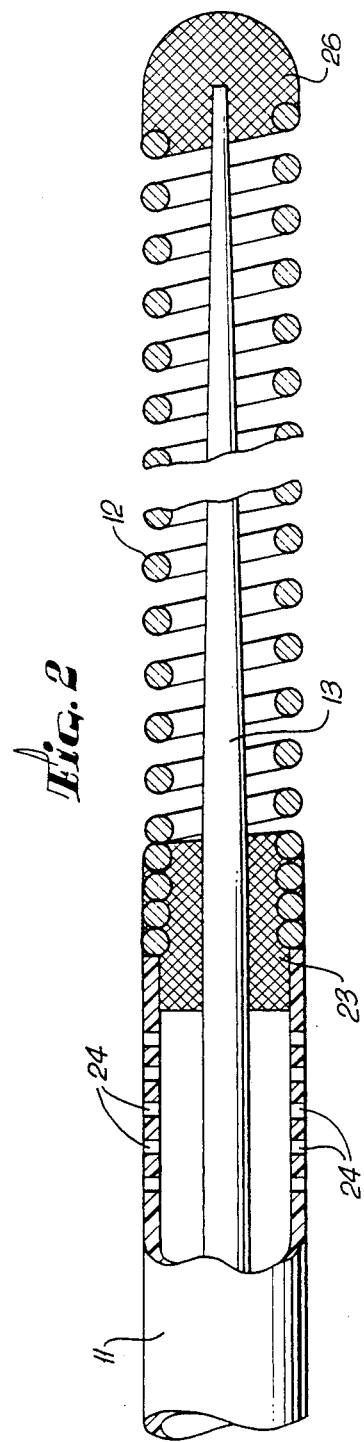

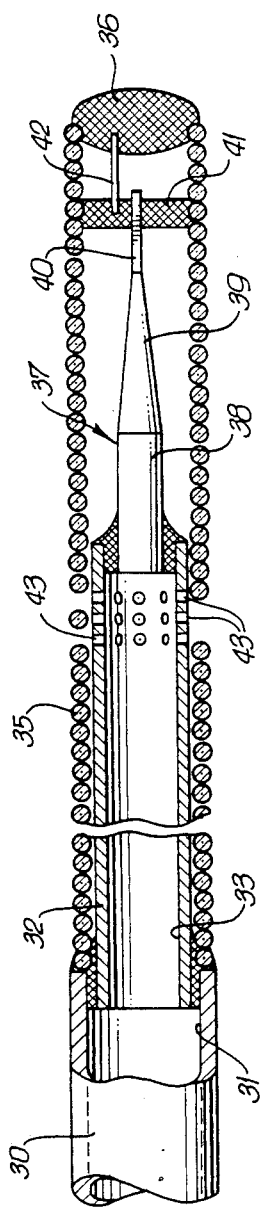
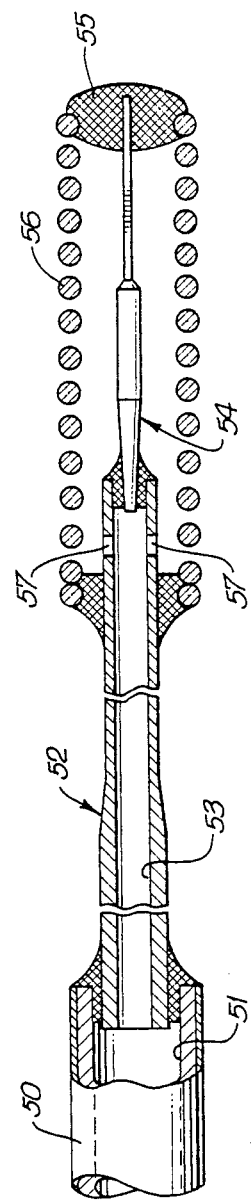
Fig. 3
Fig. 4

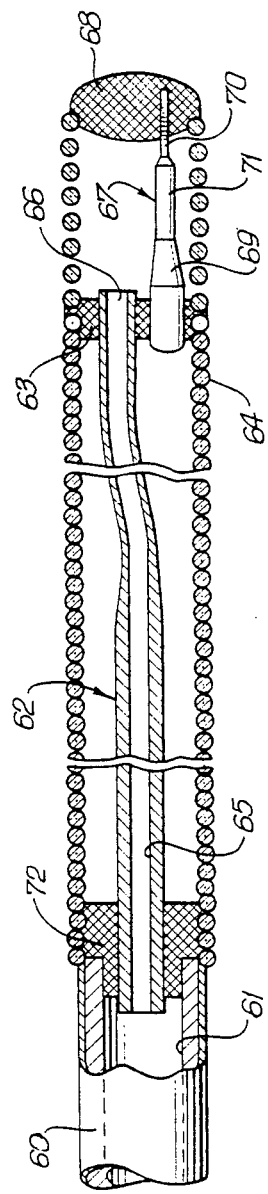
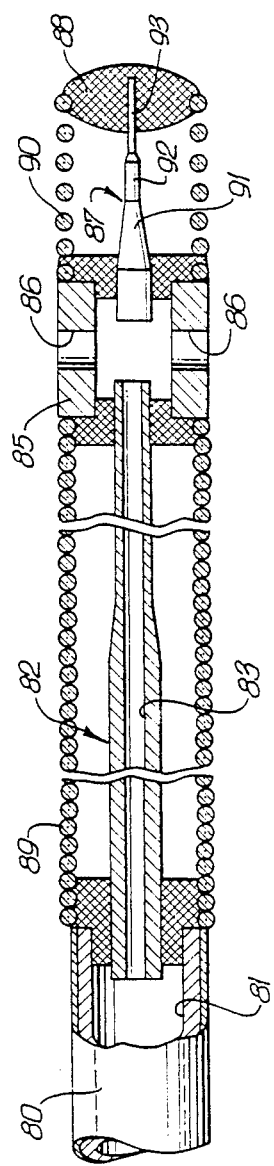
Fig. 5
Fig. 6

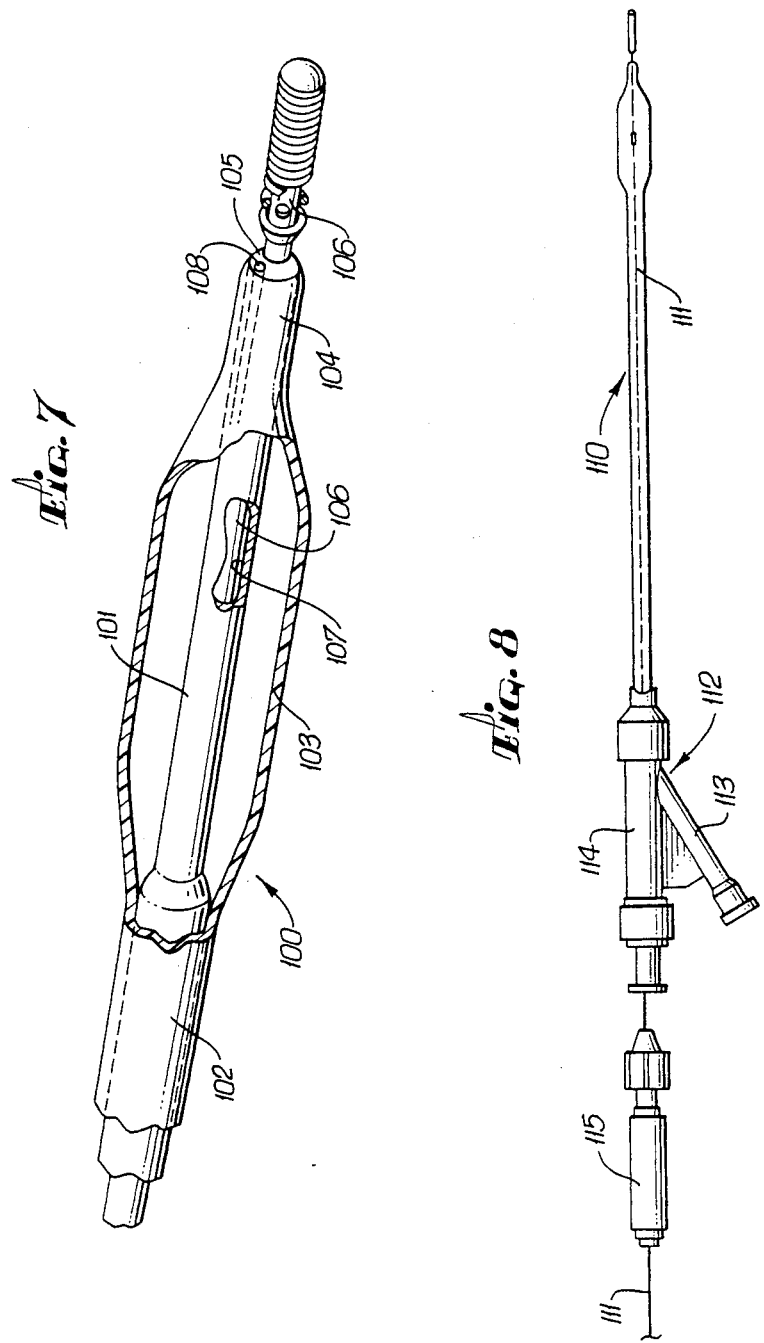

PRESSURE MONITORING GUIDEWIRE WITH A FLEXIBLE DISTAL PORTION

This application is a continuation-in-part of application Ser. No. 103,109 filed Sept. 30, 1987, now abandoned.

This invention generally relates to guiding members for the advancement of catheters within a patient's vascular system in procedures such as percutaneous transluminal coronary angioplasty (PTCA) and particularly to such guiding members which facilitate the monitoring of pressure at the distal end thereof.

In typical PTCA procedures a guiding catheter having a preformed distal tip is percutaneously introduced into the cardiovascular system of a patient and advanced therein until the distal tip thereof is in the coronary artery. A guidewire is introduced through the guiding catheter and advanced into the patient's coronary vasculature until the distal end of the guidewire crosses a lesion to be dilated. A dilatation catheter having an inflatable balloon on the distal portion thereof is advanced into the patient's coronary anatomy over the previously introduced guidewire, with the guidewire slidably disposed within an inner lumen of the dilatation catheter, until the dilatation balloon is properly positioned across the lesion. Once in position across the lesion, the balloon is inflated to a predetermined size with radiopaque liquid at relatively high pressures (e.g., greater than 4 atmospheres) to compress the atherosclerotic plaque of the lesion against the inside of the artery wall. The balloon is then deflated so that the dilatation catheter can be removed and blood flow resumed through the dilated artery.

Steerable dilatation catheters with built-in guiding members are being used with increasing frequency because the deflated profiles of such catheters are generally much smaller than conventional dilatation catheters and a smaller profile allows the catheter to cross tighter lesions and to be advanced much deeper into the patient's coronary anatomy. Additionally, the use of steerable low-profile dilatation catheters can shorten the time for the angioplasty procedures because there is no need to first advance a guidewire through the stenosis and then advance a conventional dilatation catheter over the previously placed guidewire.

Further details of dilatation catheters, guidewires, and the like for angioplasty procedures can be found in U.S. Pat. No. 4,323,071 (Simpson-Robert); U.S. Pat. No. 4,439,185 (Lundquist); U.S. Pat. No. 4,468,224 (Enzmann et al.); U.S. Pat. No. 4,516,972 (Samson), U.S. Pat. No. 4,538,622 (Samson et al.); U.S. Pat. No. 4,582,181 (Samson); U.S. Pat. No. 4,616,652 (Simpson); and U.S. Pat. No. 4,638,805 (Powell) which are hereby incorporated herein in their entirety by reference thereto.

Efforts have been made such as described in U.S. Pat. No. 4,582,181 to develop hollow guidewire systems which allow for the measurement of the fluid pressure at the distal end of the catheter from the proximal end of the catheter. However, usually such pressure sensing guidewires do not have the flexibility in the distal portion thereof to be advanced very far into a patient's vasculature, particularly the coronary arteries. What has been needed and heretofore unavailable is a guidewire which has sufficient flexibility in the distal portion thereof to be easily advanced through a patient's arteries and which can monitor from the proximal end thereof the fluid pressure within the patient's artery at the distal end of the guidewire. The present invention satisfies that need.

SUMMARY OF THE INVENTION

The present invention is directed to an improved flexible guidewire which facilitates the monitoring of fluid pressure during intravascular procedures, such as angioplasty, angiography and valvuloplasty.

The guiding catheter in accordance with the invention generally includes an elongated tubular shaft having an inner lumen axially extending therethrough and a plurality of pressure monitoring ports on the distal portion thereof in fluid communication with the inner lumen, a core member extending distally from the distal end of the tubular member, which is manually shapeable at least in the distal portion thereof, and a helical coil or other flexible body disposed about the shapeable section of the core member. The distal end of the tubular member preferably includes a short, smaller diameter inner tubular extension which contains the pressure monitoring ports.

In a presently preferred embodiment, an outer tubular extension extends from the distal end of the tubular shaft, proximal to the pressure monitoring ports in the inner tubular extension to a distal location wherein the coil or other flexible body is bonded to the core member. The distal portion of the outer tubular extension has a plurality of pressure ports which provide fluid communication between the inner lumen of the elongated tubular shaft and the ambient or exterior of the guidewire. The outer tubular extension is diametrically relatively rigid to prevent kinking but is provided with a greater degree of longitudinal flexibility than the elongated tubular shaft because it is this distal portion of the guidewire which extends out of the guiding catheter and is advanced into the patient's coronary anatomy.

The guidewire in accordance with the invention readily advances through a patient's vasculature and particularly through the coronary anatomy thereof. Moreover, the pressure monitoring from the proximal end thereof accurately represents the fluid pressure within the patient's artery at the distal end of the guidewire. These and other advantages of the invention will become more apparent from the following detailed description thereof when taken in conjunction with the accompanying drawings.

BRIEF DESCRIPTION OF THE DRAWINGS

FIG. 1 is a fragmentary centerline sectional view of a pressure monitoring guidewire embodying features of the invention;

FIG. 2 is a fragmentary centerline sectional view of an alternative embodiment to that shown in FIG. 1;

FIGS. 3–6 are fragmentary centerline sectional views of additional embodiments of pressure monitoring guidewires according to the invention;

FIG. 7 is a perspective view partially in section illustrating a low-profile dilatation catheter with a guidewire embodying features of the invention; and FIG. 8 is a plan view of a dilatation guidewire and dilatation catheter system with a two-arm adapter.

DETAILED DESCRIPTION OF THE INVENTION

FIG. 1 illustrates a guidewire embodying features of the invention which generally includes a tubular shaft 10, an outer, longitudinally flexible tubular extension 11, a helical coil 12 and a core member 13. The tubular shaft 10, is provided with an outer coating of lubricious material 14, such as Teflon, and has an inner lumen 15 axially extending therethrough. A short inner tubular extension 16 is secured within the inner lumen 15 at the distal end 17 of the tubular shaft 10 and is provided with a plurality of pressure sensing ports 20 in fluid communication with the inner lumen 15. The proximal end 21 of core member 13 is secured within the open distal end 22 of tubular extension 16.

The outer longitudinally flexible tubular extension 11 is secured at its proximal end to the distal end of tubular shaft 10 and at its distal end to core member 13 at location 23. A plurality of pressure monitoring ports 24 are provided in the distal portion of the outer tubular extension 11 which bring into fluid communication the ambient and the inner lumen 15 of tubular shaft 10.

The distal extension of core member 13 terminates short of the distal end of the coil 12 but a shapeable ribbon 25 extends through the interior of coil 12 to the rounded plug 26 on the distal end thereof. Ribbon 25 is joined at its proximal end to core 13 and the proximal end of the coil at location 23 by suitable means, such as soldering, and at its distal end to rounded plug 26.

An alternative embodiment is shown in FIG. 2 wherein the core member 13 extends to the rounded plug 26. In all other respects the embodiment is the same as that shown in FIG. 1.

The elongated tubular shaft 10 and the short tubular extension 16 are preferably formed of stainless steel hypotubing. The core 13, preferably a solid member, and shaping ribbon 25 are likewise formed of stainless steel or a cold rolled alloy of tungsten and rhenium. The shaping ribbon of the latter alloy is preferably gold plated. The coil 12 is preferably formed from a gold plated palladium-platinum-molybdenum alloy wire. The outer tubular extension 11 is preferably formed from polyimide and is preferably coated with a lubricious coating as described in copending application Ser. No. 302,584, filed Jan. 26, 1989.

Suitable dimensions of the various members of a guidewire shown in FIGS. 1 and 2 are given as follows. Typical dimensions are provided in parentheses.

The elongated tubular shaft 10 is generally about 120 to about 160 cm (140 cm) in length with an outer diameter of about 0.012 to 0.018 inch (0.015 inch) and an inner diameter of about 0.007 to about 0.013 inch (0.01 inch). The outer tubular extension 11 is about 25 to about 45 cm (33 cm) in length, with the outer diameter thereof ranging from about 0.0065 to about 0.0125 inch (0.0095 inch) and the inner diameter from about 0.0035 to about 0.0085 inch (0.006 inch). The short inner tubular extension 16 is sized to tightly fit into the distal end of tubular shaft 10 and is generally about 8 cm long. The core member 13 ranges from about 25 to about 45 cm (35 cm) in length with the tapered section thereof being about 2 to about 6 cm (2.5 cm) in length. The outer diameter of the main portion of core member 13 is about 0.004 to about 0.012 inch (0.0065 inch) with the smallest diameter of the tapered section being about 0.0015 to about 0.004 inch (0.0025 inch). The wire forming coil 12 is about 0.002 to about 0.003 inch (0.0025 inch) in diameter and the coil section is about 1.5 to 5 cm in length (3 cm) and about 0.01 to about 0.015 (0.0125 inch) in outer diameter. The pressure monitoring ports 20 and 24 generally number about 10 to about 30 (20) in each group and they are generally about 0.0015 to about 0.0045 inch (0.002 inch) in diameter. Preferably, they are equally spaced in linearly arranged groups about the periphery of the members in which they are formed. The pressure monitoring ports should be spaced distally about 20 to about 40 cm from the distal end of the tubular shaft 10. The guidewire of the invention suitable for angioplasty may have an outer diameter from about 0.010 to about 0.038 inch, whereas for valvuloplasty, the outer diameter can range from about 0.025 to about 0.045 inch.

A Tuohy-Borst adapter (not shown) may be attached to the proximal end of the tubular shaft 10 for attachment to a stopcock manifold and pressure monitoring system in a conventional manner.

The metal to metal bonding in the guidewire of the invention may be effected in a well known manner such as by welding, soldering, brazing, and the like, whereas bonding to plastic materials is preferable by means of an adhesive such as cyanoacrylate (e.g., Loctite 405).

In a typical operation of the guidewire in accordance with the invention, the guidewire is introduced into an inner lumen of a dilatation catheter and then both are advanced through a guiding catheter previously disposed within a patient's vasculature with the distal end of the guiding catheter being within the ostium or opening of the desired coronary artery. The guidewire of the invention is then advanced from the distal tip of the guiding catheter into the patient's coronary artery with the pressure monitoring ports 24 in a desired location, e.g., distal to a stenosis, so that pressure measurements may be taken prior to angioplasty procedures. The dilatation catheter may then be advanced over the guidewire until the balloon thereof crosses the stenosis where it is inflated and deflated in a normal manner to perform the dilatation. After deflation of the balloon, the guidewire of the invention is still in position with the pressure monitoring ports thereof distal to the stenosis so that further pressure measurements may be taken to determine the effectiveness of the angioplasty procedure.

FIG. 3 illustrates an alternative embodiment of the invention. As shown, the guidewire of this embodiment has an elongated tubular shaft 30 which has an axially extending inner lumen 31. A shorter and more flexible tubular extension 32 extends axially from the distal end of the tubular shaft 31 with an inner lumen 33 in axial alignment with the lumen 31 of the tubular shaft 30. The tubular extension 32 has an outer diameter slightly smaller than the inner diameter of the shaft 30 so that the proximal end thereof fits within the distal end of the shaft 30.

A flexible spring coil 35 extends in an axial direction from the distal end of tubular shaft 30 to form a flexible tip for the guidewire. Tubular extension 32 is positioned within the proximal end portion of the coil 35. A rounded plug 36 is provided at the distal end of the coil 35.

A core member 37 extends in an axial direction from the distal end of extension 32 within coil 35 but terminates short of the distal tip of coil 35. The core 21 has a cylindrical proximal section 38, a conically tapered central section 39, and a flattened end section 40 of generally rectangular cross section. The proximal end of the core 37 is secured within the distal end of the extension 32 and affixed thereto by suitable means, such as solder. The flattened distal end 40 of the core 37 is affixed to coil 35 by solder or other suitable means at location 41. Flat shaping ribbon 42 extends between the location 41 and plug 36.

A plurality of pressure monitoring ports 43 are formed in the wall forming tubular extension 32 near the distal end thereof. In the embodiment illustrated, the windings of coil 35 are spaced apart in the vicinity of the ports 43 to provide unobstructed access thereto. As shown, ports 43 extend circumferentially around the tubular extension 32 and provide fluid communication between the ambient and lumen 31 through lumen 31 and thereby facilitate measurements of pressure at the distal end of the guidewire from the proximal end thereof.

The tubular extension 32 is preferably fabricated of any suitable material which provides longitudinal flexibility and diametrical rigidity such as hypotubing formed from superelastic metals, such as nitinol or plastic materials, such as polyimide. The other components of the guidewire can be made of materials previously described. The configuration of core 37 with the shaping ribbon 42 (commonly termed "floppy") is only one possible configuration for the distal portion of the guidewire. Other configurations may be employed.

In another embodiment of the invention shown in FIG. 4, the guidewire has an elongated tubular shaft 50 with an axially extending inner lumen 51. A longitudinally flexible tubular extension 52 is secured to the distal end of the tubular shaft 50, with a lumen 53 in axial alignment with the lumen 51 of the shaft 50. Core member 54 is secured within the end of the tubular extension 52 by suitable means and extends axially to rounded plug 55. A flexible spring coil 56 is secured at its proximal end to the distal end of extension 52 and is fixed to rounded plug 55. Pressure monitoring ports 57 are provided in the wall of tubular extension 52 toward the distal end thereof.

In another embodiment of the invention shown in FIG. 5, the guidewire has an elongated tubular shaft 60 with an axially extending inner lumen 81. A tubular extension 62 is secured within the distal end of the tubular shaft 60 and extends distally to location 63 where it is soldered or otherwise joined to coil 64. The tubular extension 62 has an inner lumen 65 which communicates with the inner lumen 61 in the shaft 60 and is open at its distal end to communicate with the ambient through pressure monitoring port 66. The distal portion of extension 62 is offset from the main axis of the guidewire to accommodate core member 67 which is secured at location 63 beside the distal end of extension 62. The core member 67 extends distally to the rounded plug 68 at the distal end of the coil 64. The core member 67 has a conically tapered proximal section 69, a cylindrical central section 71, and a flattened distal end section 70 of generally rectangular cross section. The proximal end of coil section 64 is secured to the tubular extension 62 by suitable means, such as solder at location 72. The distal end of coil section 64 is secured to the rounded plug 68. As shown in FIG. 5, coil 64 has two sections: one extending over the tubular extension 62 and one extending over the core member 67. The windings at the distal end of coil section 64 are spaced apart to provide unobstructed access to the pressure monitoring port 66 at the distal end of tubular extension 62.

In another embodiment of the invention shown in FIG. 6, the guidewire has an elongated tubular shaft 80 with an axially extending inner lumen 81. A longitudinally flexible tubular extension 82 is secured to the distal end of the tubular shaft 80 with an inner lumen 83 in fluid communication with the inner lumen 81 in the tubular shaft 80. The distal end of tubular extension 82 has bonded thereto a short cylindrically shaped tube 85 which is provided with a plurality of pressure monitoring ports 86 to provide fluid communication between the ambient and the inner lumens 81 and 83. Core member 87 is secured to the short cylindrical tube 85 by suitable means such as solder and extends axially to rounded plug 88.

A spring coil 89 is secured at its proximal end by suitable means to the tubular shaft 80 and to the distal end of tubular extension 82. A short coil 90 extends between the short cylindrically shaped tube 85 and the plug 88.

Core member 87 has a conically tapered proximal section 91, a cylindrical central section 92, and a flattened distal section 93 of a generally rectangular cross section.

Operation and use of the embodiments of FIGS. 3–6 are essentially that of the embodiments shown in FIGS. 1 and 2.

The guidewire of the invention has extensive application in procedures such as angioplasty, angiography, and valvuloplasty. A pressure gradient may be obtained between the guiding catheter at the coronary ostium and the tip of the guidewire on the distal side of the lesion before, during, and after dilatation. The guidewire of the invention eliminates the need for any pressure monitoring through the lumen of the dilatation catheter which permits the catheter to be constructed with a lower profile, thus making it possible for the first time to monitor distal pressures through catheters of very low profile. Accurate pressure readings can be obtained regardless of whether the balloon is inflated or deflated. When the balloon is inflated, the guidewire will provide a "wedge pressure" reading for the coronary anatomy, possibly identifying the presence of collateral circulation distal to the lesion or identifying other circulatory anomalies. The guidewire is highly torquable and is readily steered to facilitate placement deep within the patient's cardiovascular system. Moveover, the distal portion of the guidewire, e.g., the most distal 20–40 cm thereof, will not develop a permanent curved set when passing through the curved distal tip of the guidewire catheter, which can nave a radius of curvature as small as 0.5 cm.

FIG. 7 illustrates a guidewire in accordance with the invention fixed within a low profile steerable dilatation catheter, such as the Hartzler Micro TM dilatation catheter which is manufactured and sold by the present assignee Advanced Cardiovascular Systems, Inc. The catheter 100, generally comprises an inner tubular member 101, and an outer tubular member 102 having an inflatable balloon element 103 adjacent the distal end 104 thereof. The distal end 104 of the outer tubular member 102 is preferably shrunk-fit or otherwise tightly secured to the distal end 105 of the inner tubular member 101. Guidewire 106, preferably such as that shown in FIG. 1, is disposed within the inner lumen 107 of the inner tubular member 101. A venting passageway 108 is provided between the distal ends 104 and 105 to vent air from the interior of the balloon 103.

FIG. 8 represents a dilatation catheter system including a catheter 110 and guidewire 111 such as is shown in FIG. 1. A two-arm adapter 112 s provided at the proximal end of the catheter 110 having one arm 113 for inflation and one arm 114 for guidewire 111. A torque device 115 is provided on the proximal end of the guidewire 111 to rotate the guidewire when advancing the guidewire through a patient's vasculature.

The guidewire of the invention may also be used to deliver therapeutic agents such as urokinase, streptokinase, TPA, and the like to a lesion during acute myocardial infarction (heart attack), or chemotherapeutic drugs to a tumor. A Heparin drip may be employed to eliminate any clotting of blood within the fluid passageways of the wire.

It is apparent from the foregoing that a new and improved pressure monitoring guidewire and method of using the same have been provided. While only certain presently preferred embodiments have been described in detail, as will be apparent to those familiar with the art, certain changes and modifications can be made without departing from the scope of the invention as defined by the following claims.

What is claimed is:

1. A guidewire which facilitates advancing a catheter within a patient's vasculature and which allows fluid pressure at the distal extremity of the guidewire to be determined from the proximal end thereof, comprising:
   (a) an elongated tubular member having an inner lumen extending essentially from the proximal end to the distal end thereof;
   (b) a relatively short flexible plastic tubular member which is secured by the proximal end thereof to the distal end of the elongated tubular member, which has an inner lumen in fluid communication with the inner lumen of the tubular member and which is provided with at least one pressure monitoring port;
   (c) a core member which extends distally through at least a portion of the flexible plastic tubular member and which is secured to the flexible tubular element; and
   (d) a flexible coil disposed about and secured to the core member.

2. The guidewire of claim 1 wherein pressure monitoring ports open through the wall of the flexible tubular element.

3. The guidewire of claim 1 wherein the elongated tubular member comprises a relatively long tubular shaft and a relatively short tubular extension at the distal end of the tubular shaft which connects in fluid communication the inner lumen of the elongated tubular member and the inner lumen of the flexible plastic tubular member.

4. The guidewire of claim 3 wherein the core member extends axially from the distal end of the tubular extension.

5. The guidewire of claim 4 wherein the core member extends to the distal end of the guidewire.

6. The guidewire of claim 4 wherein the core member terminates proximally of the distal end of the guidewire and a shaping ribbon extends from the core member to the distal end of the guidewire.

7. The guidewire of claim 4 wherein the tubular shaft has a length of about 120 to about 160 cm and wherein pressure monitoring ports open to the exterior of the guidewire are positioned about 20 to about 40 cm beyond the distal end of the tubular shaft.

8. The guidewire of claim 1 wherein the flexible coil extends distally from the distal end of the tubular element.

9. In a steerable balloon dilatation catheter assembly having an elongated tubular body with an inflatable balloon near the distal end thereof and a guidewire fixed therein the improvement which comprises:
   (a) an elongated tubular member having an inner lumen extending essentially from the proximal end to the distal end thereof;
   (b) a relatively short flexible plastic tubular element which is secured by the proximal end thereof to the distal end of the elongated tubular member, which has an inner lumen in fluid communication with the inner lumen of the tubular member and which is provided with at least one pressure monitoring port distal to the balloon attached thereto;
   (c) a core member which extends distally through at least a portion of the flexible plastic tubular element and which is secured at the proximal end thereof to the flexible tubular element;
   (d) a flexible coil member disposed about and secured to the portion of the core member which extends out of balloon.

10. The guidewire of claim 1 wherein the distal portion thereof can pass through a radius of curvature of 0.5 cm without developing a permanent set.

* * * * *

UNITED STATES PATENT AND TRADEMARK OFFICE
CERTIFICATE OF CORRECTION

PATENT NO. : 4,953,553
DATED : September 4, 1990
INVENTOR(S) : William S. Tremulis It is certified that error appears in the above-identified patent and that said Letters Patent is hereby corrected as shown below:

Column 3, line 2: "10," should be -- 10 --.

Column 6, lines 37-38: "Move-over" should be -- Moreover --.

Column 6, line 61: "112 s" should be -- 112 is --.

Column 6, line 41: "nave" should be -- have --.

Signed and Sealed this

Fifth Day of May, 1992

Attest:

DOUGLAS B. COMER

Attesting Officer

Acting Commissioner of Patents and Trademarks